United States Patent
Fischer et al.

[11] Patent Number: 5,939,328
[45] Date of Patent: Aug. 17, 1999

[54] METHOD FOR THE DETERMINATION OF IODIDE

[75] Inventors: Wolfgang Fischer, Darmstadt; Thomas Groh, Kelsterbach; Stefanie Beil, Mörfelden, all of Germany

[73] Assignee: Merck Patent Gesellschaft Mit Beschrankter Haftung, Germany

[21] Appl. No.: 08/894,926

[22] PCT Filed: Feb. 24, 1996

[86] PCT No.: PCT/EP96/00774

§ 371 Date: Aug. 28, 1997

§ 102(e) Date: Aug. 28, 1997

[87] PCT Pub. No.: WO96/27794

PCT Pub. Date: Sep. 12, 1996

[30] Foreign Application Priority Data

Mar. 4, 1995 [DE] Germany .......................... 195 07 685

[51] Int. Cl.$^6$ .................................................. G01N 33/52
[52] U.S. Cl. ........................... 436/125; 436/63; 436/124; 436/129; 436/166; 436/174; 436/175; 436/177
[58] Field of Search ............................. 436/63, 124, 125, 436/129, 166, 174, 175, 177

[56] References Cited

U.S. PATENT DOCUMENTS 3,121,615  2/1964  Price ......................................... 23/254
4,900,682  2/1990  Fischer et al. ......................... 436/129

FOREIGN PATENT DOCUMENTS 0322631   7/1989   European Pat. Off. .
9222806  12/1992   WIPO .

OTHER PUBLICATIONS

Davies et al. "Determination of Peracids in the Presence of a Large Excess of Hydrogen Peroxide Using a Rapid & Convenient Spectrophotometric Method", Analyst, Sep. 1988, vol. 113 pp. 1477–1479.

Yaqub et al "Spectrophotometric determination of iodide in blood and urine", JPMA, J. Pak. Med. Assoc. 1979, 29(11) 249–50. Abstract only.

Yabu et al "Measurement of iodide in urine", Eiyo Asesumento (1988) 5(2) 179–83. Abstract only.

*Primary Examiner*—Jill Warden
*Assistant Examiner*—S. Carrillo
*Attorney, Agent, or Firm*—Millen, White, Zelano, & Branigan, P.C.

[57] ABSTRACT

A method for the determination of iodide in aqueous solutions, preferably in urine. The process is characterized in that the sample solution is admixed with a chromogen and a peracid solution and the color reaction is evaluated visually or photometrically. In the determination of iodide in urine, the sample is pretreated by means of a purified activated carbon.

14 Claims, No Drawings

METHOD FOR THE DETERMINATION OF IODIDE

The invention relates to methods and means for the determination of iodide in aqueous solutions, preferably in urine.

BACKGROUND OF THE INVENTION

In clinical diagnosis, the determination of iodide in the urine plays an important role in monitoring the function of the thyroid gland. The determination of iodide in foodstuffs and fodder is also becoming increasingly important. Suitable rapid methods which can be used routinely have hitherto not been described for the determination of iodide in urine.

In most known methods, a pretreatment of the urine is carried out either by treatment with a strong acid or by ashing at high temperatures. This is followed by the determination of iodide by measurement of the reduction of cerium (IV) ions to cerium (III) ions by the catalytic action of iodide (Sandell-Kolthoff reaction). The pretreatment with strong acids (potassium chlorate in 70% perchloric acid) or the dry ashing of the urine with potassium carbonate serves to remove substances which can interfere in the reduction of the cerium ions. This results in the formation of toxic perchloric acid vapors and the perchlorates which are likewise formed are known to be explosive.

Anal. Chim. Acta 282, 87 (1993) describes a method for the determination of iodide using chlorpromazine and hydrogen peroxide, but this is very susceptible to interference by many substances which occur especially in urine and also in foodstuffs and fodder. Furthermore, DE-A 37 43 224 discloses a method for the determination of peracids, wherein a chromogen and iodide are added to the sample solution. However, those skilled in the art could not deduce from this publication that this reaction can be used for the detection of iodide.

SUMMARY OF THE INVENTION

It is an object of the invention to provide a simple and rapid test for the determination of iodide by means of which even untrained personnel can determine without difficulty even small amounts of iodide in aqueous solutions semi-quantitatively or even quantitatively, without rigid pretreatment measures being required and without the formation of toxic substances.

The invention provides a method for the determination of iodide in aqueous solutions which is characterized in that the sample solution is admixed with a chromogen and a peracid solution and the color reaction is evaluated visually or photometrically. For the determination of iodide in urine, the urine sample is preferably pretreated by means of a purified activated carbon. It is here advantageous if the purified activated carbon is present in an extraction column.

The invention further provides means for the determination of iodide in aqueous solutions, which comprise a chromogen, a peracid solution and, if desired, an extraction column containing an activated carbon.

It has been found that the method of the invention is less susceptible to interference and can be carried out significantly more quickly than the known methods for the determination of iodide in urine. Iodide concentrations down to 6 $\mu$g/dl can still be detected in the presence of a high anionic matrix concentration. In aqueous solutions without an organic matrix, the detection limit for iodide is 0.2 $\mu$g/dl.

DETAILED DESCRIPTION OF THE INVENTION

For the process of the invention, chromogens used can be all chromogens known in the literature which are oxidizable in the presence of peracids using iodide as catalyst. Suitable are preferably aromatic amines such as o- and p-phenylenediamine, benzidine and benzidine derivatives, in particular tetramethylbenzidine. The concentration of the chromogen should be in the range from 1 to 5 mM, preferably about 2.5 mM.

Peracid solutions are, for example, aqueous solutions of peracetic acid, perpropionic acid, perbutyric acid, perbenzoic acid, etc., preferably an aqueous peracetic acid solution. The concentration of this solution should be in the range from 1 to 5%, preferably about 2.5%.

The means of the invention can either consist of two solutions, a peracid solution and a solution of a chromogen, or apart from the peracid solution the chromogen can, if desired together with an organic acid, be in the form of an absorbent matrix impregnated therewith.

Absorbent matrices which can be used are all those which are customarily used for such rapid tests. Most widespread is the use of filter paper, but other absorbent cellulose, glass fiber or plastic products can also be used. The absorbent supports, preferably filter paper, are impregnated in a manner known per se with impregnation solutions comprising the chromogen and, if desired, further necessary reagents. The impregnated and dried papers can be processed into square or rectangular zones which in turn can be glued or sealed in a manner known per se onto plastic films, paper strips or metal strips.

The absorbent supports can also be applied in strip form to a plastic tape prior to impregnation and after impregnation cut perpendicular to the strip direction to form convenient bars.

To allow the reaction to proceed in an optimum pH range, the chromogen solution comprises, if desired, buffer substances. If the determination of the iodide is carried out by means of a matrix impregnated with the substances required, the presence of buffer substances is likewise advantageous.

Possible buffer substances are those which can maintain a pH in the range from 3 to 7 and which do not interfere with the detection reaction. The buffer concentration to be used depends on the pH of the sample solution and on any free acids or bases present therein. Suitable buffers are the customary salts such as citrates, phosphates, borates, etc. Preference is given to using solid organic acids such as citric acid, malonic acid, succinic acid and their salts, in particular citric acid. In place of a ready-to-use buffer solution, it is also possible to use commercial buffer concentrates.

If tetramethylbenzidine is used as chromogen, the most intense color is reached at a pH of about 4. Buffer solutions having pH values up to 7 can likewise be used, but somewhat poorer detection limits then result.

In the determination of iodide in urine it is important that the sample solution is pretreated by means of activated carbon, in particular with a purified activated carbon. Since interfering sulfur-containing substances on the commercial activated carbons have an adverse effect on the color reactions, purification is generally necessary. For this purpose, the activated carbon is treated with a 1 N hydrochloric acid, followed by conditioning with the buffer solution used in the determination.

Since the activated carbon is preferably placed in a column, the pore size of the activated carbon should be in the range from 50 to 150 $\mu$m. In the case of smaller pores, the permeability for aqueous solutions is restricted, in the case of larger pores the adsorption properties of the activated carbon become poorer. The extraction column comprises from about 0.1 to 0.4 g, preferably 0.2 g, of activated carbon for one determination. Of course, the determination can also be carried out by a batch method.

A determination of iodide in urine with the aid of an extraction column containing activated carbon is carried out by introducing a urine sample diluted with buffer solution onto the conditioned column, this sample then being discarded. Subsequently, the diluted urine sample to be analyzed is then purified by means of the column and collected in a measuring vessel or a cuvette. The urine sample thus pretreated is admixed with the chromogen solution and then with the peracid solution and the color reaction is evaluated by means of a color scale or photometrically after a prescribed time of, for example, one minute. The measurement range for iodide in the process of the present invention is from 6 to 100 $\mu$g/dl of iodide. In the iodide determination using an absorptive support, the measurement range is 20–200 $\mu$g/dl of iodide.

A sample preparation using activated carbon is omitted, for example, in the determination of iodide in mineral water, seawater, table salt, etc. In the cases in which an interfering matrix has to be removed or in the presence of substances which have their own color and thus make difficult the photometric or visual evaluation, e.g. in certain foodstuffs and fodder, including the case of milk, a sample preparation is required.

EXAMPLES

Example 1

Reagent Solutions

Preparation of the chromogen solution 600 mg of tetramethylbenzidine are dissolved in 1000 ml of ethanol (2.5 mM).

The ready-to-use buffer solution (pH 4) comprises 11.7 g of citric acid, 4.4 g of sodium hydroxide and 1.6 g of hydrogen chloride in 1000 ml of water.

The peracid solution comprises 2.5 g of peracetic acid in 100 ml of water.

Example 2

Determination of Iodide in Urine a) Sample preparation

1 N hydrochloric acid and the buffer solution indicated in Example 1 are introduced in succession onto an extraction column comprising 0.2 g of activated carbon. 2 ml of a urine sample diluted with buffer solution (1 ml of urine, 4 ml of buffer solution) are introduced onto the column and discarded. Subsequently, a further 2 ml of the diluted urine sample is introduced onto the column and collected in a measuring vessel.

b) Carrying out the determination

The urine sample obtained is admixed with 200 $\mu$l of a 2.5 mM tetramethylbenzidine solution and then with one drop of a 2.5% peracetic acid solution. Corresponding to the iodide concentration, a color reaction from green to blue takes place, which is compared with a color scale after one minute.

For the photometric evaluation, the solution is placed in a 10 mm cuvette and the absorption maximum is measured at 646 nm.

Example 3

Production of a Test Bar 1.5 g of tetramethylbenzidine and 2.5 g of citric acid are dissolved in succession while stirring in a mixture of 500 ml of ethanol and 100 ml of water.

A 6 mm wide strip of paper which is glued onto an 8 cm wide white PVC film as support is impregnated with the solution comprising chromogen (amount applied: 1 ml of impregnation solution per meter of paper). After drying, the film is cut into 6 mm wide strips (test bars).

One drop of a 2.5% peracetic acid is added to the urine sample prepared in accordance with Example 2a) and the mixture is shaken. The test bar is immediately dipped in for about one second. Excess solution is shaken off. After about 10 seconds more, comparison is made with a color scale. the following iodide concentrations in urine can be distinguished by different blue coloration of the reaction zone: 20, 50, 100, 200 $\mu$g/dl.

We claim:

1. A method for the determination of iodide in an aqueous solution, which comprises:

pretreating the aqueous solution by purified activated carbon, admixing the aqueous solution, a chromogen and a peracid solution such that any iodide present in the aqueous solution catalyzes a color reaction between the chromogen and peracid, and making a visual or photometric evaluation of the color reaction to provide a determination of iodide in the solution, wherein the aqueous solution is a urine sample.

2. The method of claim 1, wherein the urine sample is pretreated in an reaction column containing said purified activated carbon.

3. The method of claim 1, wherein the method detects an iodide concentration down to 0.2 $\mu$g/dl.

4. The method of claim 1, wherein the chromogen is o-phenylenediamine, p-phenylenediamine, benzidine or tetramethylbenzidine.

5. The method of claim 1, wherein the chromogen is admixed in an amount to provide a concentration of 1 to 5 mM in the aqueous solution.

6. The method of claim 1, wherein the peracid solution contains peracetic acid, perpropionic acid, perbutyric acid or perbenzoic acid.

7. The method of claim 1, wherein the peracid solution contains peracetic acid.

8. The method of claim 1, wherein the chromogen is tetramethylbenzidine and the peracid solution is a solution of peracetic acid.

9. The method of claim 1, wherein the chromogen is provided in the form of an absorbent matrix impregnated with the chromogen and, optionally, an organic acid.

10. The method of claim 1, wherein the aqueous solution further comprises a buffer.

11. The method of claim 2, wherein the method detects iodide in a concentration range of 6–100 $\mu$g/dl.

12. The method of claim 9, wherein the absorb matrix is filter paper.

13. The method of claim 10, wherein the buffer is citric acid.

14. The method of claim 12, wherein the matrix is impregnated with tetramethylbenzidine as the chromogen and citric acid buffer.

* * * * *